(12) United States Patent
Marcum

(10) Patent No.: US 7,485,629 B2
(45) Date of Patent: *Feb. 3, 2009

(54) COMPOSITION AND METHOD FOR TREATMENT OF JOINT DAMAGE

(75) Inventor: Frank D. Marcum, Versailles, KY (US)

(73) Assignee: ArthroDynamic Technologies, Animal Health Division, Inc., Lexington, KY (US)

( * ) Notice: Subject to any disclaimer, the term of this patent is extended or adjusted under 35 U.S.C. 154(b) by 229 days.

This patent is subject to a terminal disclaimer.

(21) Appl. No.: 11/015,137

(22) Filed: Dec. 17, 2004

(65) Prior Publication Data

US 2006/0135470 A1    Jun. 22, 2006

Related U.S. Application Data

(63) Continuation-in-part of application No. 10/686,918, filed on Oct. 16, 2003, now Pat. No. 6,979,679.

(60) Provisional application No. 60/419,009, filed on Oct. 16, 2002, provisional application No. 60/487,861, filed on Jul. 16, 2003.

(51) Int. Cl.
*A01N 43/04* (2006.01)
*A61K 31/70* (2006.01)

(52) U.S. Cl. .......................... 514/52; 514/62

(58) Field of Classification Search ........................ None
See application file for complete search history.

(56) References Cited

U.S. PATENT DOCUMENTS

| | | | |
|---|---|---|---|
| 3,683,076 A | 8/1972 | Rovati | |
| 3,697,652 A | 10/1972 | Rovati et al. | |
| 4,782,046 A | 11/1988 | Brown et al. | |
| 4,801,619 A | 1/1989 | Lindblad | |
| 4,808,576 A * | 2/1989 | Schultz et al. | 514/54 |
| 4,870,061 A * | 9/1989 | Speck | 514/62 |
| 5,364,845 A | 11/1994 | Henderson | |
| 5,587,363 A | 12/1996 | Henderson | |
| 5,840,715 A | 11/1998 | Florio | |
| 5,916,565 A | 6/1999 | Rose et al. | |
| 5,922,692 A | 7/1999 | Marino | |
| 6,255,295 B1 | 7/2001 | Henderson et al. | |
| 6,432,929 B1 | 8/2002 | Stone | |
| 6,476,005 B1 | 11/2002 | Petito | |
| 6,492,349 B1 | 12/2002 | Henderson | |
| 6,506,785 B2 | 1/2003 | Evans et al. | |
| 6,608,041 B2 | 8/2003 | Hammerly | |
| 6,645,482 B2 | 11/2003 | Theoharides | |
| 6,906,044 B2 | 6/2005 | Hermida | |
| 6,949,525 B2 | 9/2005 | Hermida | |
| 6,979,679 B2 * | 12/2005 | Marcum | 514/53 |

| | | | |
|---|---|---|---|
| 2002/0068718 A1 * | 6/2002 | Pierce | 514/54 |

FOREIGN PATENT DOCUMENTS

| | | |
|---|---|---|
| GB | 2317109 A | 3/1998 |
| GB | 2317109 A | 3/1998 |
| WO | WO 01/32188 A1 | 5/2001 |
| WO | WO 03/041724 A1 * | 6/2003 |

OTHER PUBLICATIONS

Dorna and Guerrero, Journal of Equine Veterinary Science 1998, vol. 18, No. 9, abstract only.*
Bassleer et al., 1998, "Stimulation of Proteglycan Production by Glucosamine Sulfate in Chondrocytes Isolated from Human Osteoarthritic Articular Cartilage in Vitro," Osteoarthritis and Cartilage, vol. 6, pp. 427-434.
Bucci et al., 1994, "Glucosamine Salts and Chondroitin Sulfates," Townsend Letter for Doctors, pp. 52-54.
Capps et al., 1966, "Hexosamine Metabolism," Biochimica et Biophysica ACTA, 127:194-204.
Coleman et al., 1999, "Characterization of the Effect of High Molecular Weight Hyaluronan on Trans-Synovial Flow in Rabbit Knees," Journal of Physiology, 514.1, pp. 265-282.
Coleman et al., 1997, "Hyaluronan Secretion into the Synovial Cavity of Rabbit Knees and Comparison with Albumin Turnover," Journal of Physiology, 503.3, pp. 645-656.
Coleman et al., 2000, "Role of Hyaluronan Chain Length in Buffering Interstitial Flow Across Synovium in Rabbits," Journal of Physiology, 526.2, pp. 425-434.
Day et al., 2002, "Hyaluronan-Binding Proteins: Tying up the Giant," The Journal of Biological Chemistry, vol. 277, No. 7, pp. 4585-4588.

(Continued)

*Primary Examiner*—Shaojia Anna Jiang
*Assistant Examiner*—Layla Bland
(74) *Attorney, Agent, or Firm*—Sutherland Asbill & Brennan LLP

(57) ABSTRACT

The invention provides compositions useful for the treatment and/or prevention of damage to diarthrodial (synovial) joints and, in particular, traumatic synovitis, inflammation of the synovial membrane, and damage to the articular cartilage of the joint. Specifically, provided are compositions specially formulated for intra-articular and/or parenteral use in the treatment and/or prevention of traumaticsynovitis and/or damage to articular cartilage. Compositions adapted specifically for post surgical joint lavage or treatment and/or prevention of inflammatory arthritis, osteoarthritis (OA) and/or degenerative joint disease (DJD) are also provided. Compositions adapted for intra-articular and/or systemic administration comprised of therapeutic amounts of: chondroitin sulfate and hyaluronan (hyaluronic acid) are provided.

9 Claims, No Drawings

OTHER PUBLICATIONS

Dorna et al., 1998, "Effects of Oral and Intramuscular Use of Chondroitin Sulfate in Induced Equine Aseptic Arthritis."

Hinderlich et al., 2000, "Molecular Cloning and Characterization of Murine and Human N-acetylglucosamine Kinase," Eur. J. biochem., 267:3301-3308.

Johnson et al., 2001, "Chondroitin Sulfate," Continuing Education Module from the New Hope Institute of Retailing.

McIlwraith, "Traumatic Joint Injuries and Disease," http://www.equineortho.colostate.edu/questions/tjd.htm.

Murray M.:"Glucosamine sulfate: effective osteoarthritis treatment." Amer. J. Nat. Med. 1994; Sep. 10-14.

Sabaratnam et al., 2002, "Interactive Effect of Chondroitin Sulphate C and Hyaluronan on Fluid Movement Across Rabbit Synovium," Journal of Physiology, 540.1, pp. 271-284.

Schiavinato et al., 2002, "Comparison of the Effects of Intra-Articular Injections of Hyaluronan and Its Chemically Cross-Linked Derivative (Hylan G-F20) in Normal Rabbit Knee Joints," Clinical and Experimental Rheumatology, 20:445-454.

Shikhman et al., 2001, "N-Acetylglucosamine Prevents IL-1beta-Mediated Activation of Human Chondrocytes," The American Association of Immunologists.

Tersariol et al., 2002, "Proteinase Activity Regulation by Glycosaminoglycans," Brazilian Journal of Medical and Biological Research, 335:135-144.

Tesoriere et al., 1972, "Intestinal Absorption of Glucosamine and N-Acetylglucosamine," Experientia 28:770-1.

Todhunter et al., 1993, "Effects of Exercise and Polysulfated Glycosaminoglycan on Repair of Articular Cartilage Defects in the Equine Carpus," Journal of Orthopaedic Research, 11:782-795.

Heart et al., 2002, "Glucose Transport by Osmotic Shock and Vanadate is Impaired by Glucosamine," Biochem Biophys Res Commun; 292:308-11.

de Mattei et al., 2002, "High Doses of Glucosamine-HC1 have Detrimental Effects on Bovine Articular Cartilage Explants Cultured in vitro," Osteoarthritis-Cartilage.; 10(10):816-25.

Breborowicz et al., 1998, "The effect of N-acetylglucosamine as a substrate for in vitro synthesis of glycosaminoglycans by human peritoneal mesothelial cells and fibroblasts," Adv Perit Dial; 14:31-5.

Vide;a Doma I. DVM and C. Guerrero DVM, Effects of Oral and Intramuscular use of Chondroitin Sulfate in Induced Equine Aseptic Arthritis, Journal of Equine Veterinary Science, Sep. 1998.

* cited by examiner

COMPOSITION AND METHOD FOR TREATMENT OF JOINT DAMAGE

CROSS-REFERENCE TO RELATED APPLICATIONS

This patent application claims continuation-in-part priority to U.S. application Ser. No. 10/686,918, filed on Oct. 16, 2003, issued as U.S. Pat. No. 6,979,679, which claims priority to U.S. Provisional Application Ser. No. 60/419,009, filed on Oct. 16, 2002 and U.S. Provisional Application Ser. No. 60/487,861, filed on Jul. 16, 2003, the entire contents of which are all incorporated by reference herein.

FIELD OF INVENTION

The present invention is generally directed to compositions useful for the treatment and/or prevention of damage to diarthrodial (synovial) joints and, in particular traumatic synovitis, inflammation of the synovial membrane, and damage to the articular cartilage of the joint. Specifically, the invention relates to compositions specially formulated for intra-articular and parenteral use in the treatment and/or prevention of traumatic synovitis and damage to articular cartilage, e.g., for post surgical joint lavage or treatment and/or prevention of inflammatory arthritis, osteoarthritis (OA) and/or degenerative joint disease (DJD).

BACKGROUND OF THE INVENTION

Diarthrodial or synovial joints allow movement and transfer of load between bones. These two critical functions play a major role in athletic performance and disease or injury of these joints, in turn, has a major impact on athletic performance in man and in animals. For example, one of the most important causes of lameness among equine athletes is primary joint disease of the diathrodial or synovial joints. In the past 25 years much knowledge has been gained regarding the treatment and/or prevention of disease processes affecting synovial joints and, in particular, in the understanding of disease and trauma of articular cartilage (see, McIlwraith & Trotter, "JOINT DISEASE IN THE HORSE", W. B. Saunders, 1996 (ISBN 0-7216-5135-6)).

As a brief overview, the highly mobile diarthrodial joints of the body have similar structures and components including: the joint capsule, or outer membrane, which encases the joint; collateral ligaments which are intra-capsular and provide support and stability for the joint (these work in conjunction with supporting muscle, other extra-capsular ligaments, tendons and connective tissue); articular cartilage which covers the ends of the articulating bones within the joint; subchondral bone which provides structural support to the overlying articular cartilage; the synovium, a modified mesenchyme; and synovial fluid which lubricates and nourishes the joint surfaces.

The joint capsule consists of a thick fibrous portion, which is lined by a thinner subsynovium (lamina propria) and the synovium (synovial membrane). The synovium or inner lining of the joint capsule consists of cells, synoviocytes, which have both secretory and phagocytic functions. Synovial lining cells synthesize hyaluronan (hyaluronic acid or HA) that is secreted into the synovial fluid, which occupies the intra-articular space.

Synovial fluid is essentially an ultrafiltrate of plasma with the exception of the hyaluronan (a non-sulfated glycosaminoglycan lacking a protein core) secreted by the synovium. Synovial fluid is normally highly viscous due to its hyaluronan content and plays a crucial role in maintaining healthy cartilage and protecting the joint surface.

Hyalauronan is also known as hyaluronic acid (HA). This important glycosaminoglycan (GAG) is an integral part of both synovial fluid and articular cartilage. Within the articular cartilage, hylauronan provides viscoelastic properties allowing ease of motion between opposing surfaces and increasing compressive resistance. Within the synovium, hyaluronic acid, as a component of synovial fluid, provides an effective barrier regulating the introduction of plasma components. Under normal conditions, the body will synthesize sufficient amounts of base components to maintain and grow healthy articular cartilage, while limiting the production and release of destructive proteinases, inflammatory mediators and atabolic enzymes.

Articular cartilage is a matrix of proteoglycans, chondrocytes, and collagen, which has a translucent or glasslike (hyaline) appearance due primarily to its high water content. Articular cartilage absorbs shock from mechanical forces and provides a smooth surface so that bone ends may glide easily across one another. Articular cartilage is comprised of about 70% water (up to about 80% water in neonatal animals), collagen, proteoglycans, and chondrocytes. Most of the collagen found in articular cartilage is type II collagen which provides tensile strength to the cartilage. This versatile protein provides elasticity and the structural framework of the cartilage matrix.

Proteoglycans, the other major solid component of the articular cartilage matrix consist of one or more glycosaminoglycan chains covalently bonded to a protein core. Due to their dense negative ion content, these molecules are able to attract and retain water within the cartilage formation specifically for lubrication. Proteoglycans provide the unique mechanical properties for resiliency and recovery under compressive forces.

The major proteoglycans found in cartilage are chondroitin sulfate, dermatan sulfate, keratan sulfate and hyaluronan. (Heparin sulfate is also a proteoglycan, although it is not a component of articular cartilage.) Newer names for proteoglycans sometime reference function of the core protein within the molecule, e.g., aggregan (found in chondroitin sulfate and keratin sulfate), a large proteoglycan aggregates with hyaluronin, or location, e.g., decorin (dermatan sulfate), which decorates type I collagen fibrils, or to primary structure, biglycan which has two glysoaminoglycan chains.

Chondrocytes are active cells within the cartilage matrix, which manufacture new collagen and proteoglycan molecules while excreting enzymes, which aid in removal of damaged cartilage and proteoglycans.

Under normal conditions, the body maintains the synovial joint in state of homeostasis through a variety of complex hormonal and mechanical feedback mechanisms. Two types of insult or injury can upset the delicate homeostatic balance. Repeated trauma or stress (slow chronic insult) to the joint during everyday use, e.g., athletic training or performance, is often the inciting cause of joint inflammation and loss of homeostasis. Initially, such stress results in only soft tissue inflammation in the form of synovitis or capsulitis (e.g., traumatic synovitis). Cartilage damage may or may not initially be present in the early stages of stress related injury or inflammation. However, the release of inflammatory mediators into the joint such as prostaglandins, cytokines, lysosomal enzymes and free radicals can lead to damage of articular cartilage and can cause cartilage degradation and can lead to development of degenerative joint disease (DJD).

A second type of insult or injury, the osteochondral defect, e.g., a chip fracture, is often associated with an acute mechanical failure or traumatic injury, e.g., an acute racing or training injury, although, such a fracture can be due to secondary complications associated with chronic DJD. Under this scenario, the lesion often starts as a traumatically induced defect in the articular cartilage. This may occur as a fragmentation of the original tissue from the joint margins or other defect which compromises the surface and integrity of the articular cartilage. Exposure of the supporting subchondral bone to synovial fluid and the intermittent pressures of the synovial fluid generated by repeated joint movement (repeated stress and trauma of training or racing) can lead to progressive subchondral bone sclerosis and eventual dislodging of the chip or bone fragment. Left untreated, the resulting damage often becomes progressive and DJD results (see, e.g., Nixon et al., "EQUINE FRACTURE REPAIR", W. B. Saunders Co., 1996 (ISBN 0-7216-6754-6)).

Under either scenario, once compromised, the damage to articular cartilage is usually permanent. In general, once damaged, therapy is normally directed at limiting or reducing joint inflammation, limiting the release of inflammatory mediators, removal of the inciting cause (e.g., the chip) and replacement of synovial fluid components. These measures are combined with a period of rest to allow for healing and fibrocartilage deposition at the affected area. The long term therapeutic objective is directed at slowing the progression of degenerative processes and controlling the clinical signs of DJD. Prevention is often aimed at limiting joint inflammation before damage to cartilage occurs and in providing proper nutritional support.

There have been countless therapeutic approaches for management of joint disease. Chief among these is the nutritional supplementation of metabolic precursors to the diet to aid in the biosynthesis of proteoglycans, GAG's, hyaluronan, and collagen. Nutritional supplements or "nutraceuticals" such as COSEQUIN® (see, U.S. Pat. Nos. 5,364,845 and 5,587,363) and GLC 5500® (see, PCT International Publication No. WO 0132188 A1) are recommended for oral supplementation of the diet for providing the necessary metabolic precursors for aiding the body in reparation of joint injury.

In particular, a list of metabolic precursors which have been used as oral supplementation for the production of articular cartilage are found e.g., in PCT International Publication No. WO 0132188 A1 to Madere. These oral supplements include, chondroitin sulfate, a glycosaminoglycan polysaccharide, which is a primary component of articular cartilage comprising an amino sugar and an organic acid or sugar. Chondroitin sulfate is broken down into sulfate disaccharides and N-Acetyl galactosamine. D-Glucuronic acid is a key substrate comprising one half of the hyaluronan molecule, the other being N-Acetyl D-glucosamine. Chondroitin sulfate, as CS4 and CS6 within the body, are thought to be an essential glycosaminoglycans which bind water to the articular cartilage matrix and are necessary for the formation of proteoglycans.

Another oral supplement, glucosamine, as glucosamine 5-phosphate, is naturally occurring within the body and is a component in the biosynthesis of glycosaminoglycans, proteoglycans, hyaluronan, and collagen. Glucosamine is available in exogenous forms, glucosamine sulfate sodium, glucosamine hydrochloride and N-Acetyl D-Glucosamine. These forms are reported to be orally bioavailable in mammals.

Methylsulfonymethane (MSM), also used in oral supplements, is an integral part of hemoglobin and body tissue, and is essential for the synthesis of connecting tissues, collagen and the essential amino acids methionine and cysteine. Sodium ascorbate is an oral supplement that needed for collagen production and aids in the body's ability to utilize manganese. In theory, oral supplementation and subsequent biosynthesis of the metabolic precursors aid in the production of new articular cartilage while aiding in regulating the damaging effects of destructive enzymes. Exogenous glucosamine is believed to allow the body to exceed the natural rate-limiting thresholds whereby glucosamine becomes the stimulant in the production of proteoglycans and GAGs. Exogenous oral glucosamine is also believed to stimulate chondrocytes to produce more collagen and enhance articular cartilage metabolism.

Numerous other disclosures also suggest the introduction of nutritional supplements as therapy for the treatment of connective tissues. U.S. Pat. No. 3,683,076 to Rovati et al. teaches that glucosamine sulfates are useful to treat arthritic conditions. U.S. Pat. No. 3,697,652 to Rovati et al. discloses that N-acetyl glucosamine can be used to treat degenerative afflictions of the joints. U.S. Pat. Nos. 5,364,845, 5,587,363 and 6,492,349 (to Henderson) show that glucosamine, chondroitin and manganese are used to protect and repair connective tissue. In U.S. Pat. No. 5,840,715 to Florio, N-acetyl glucosamine sulfate, chondroitin sulfate, gamma linolenic acid ercosapentaenoic acid and docosahexaneoic acid, and manganese aspartate are combined to treat arthritis symptoms. U.S. Pat. No. 5,916,565 to Rose et al. teaches a composition comprised of D-glucosamine hydrochloride, chondroitin sulfate, cayenne, ginger, turmeric, yucca, Devil's Claw, nettle leaf, Black Cohosh, alfalfa, and celery seeds to repair and maintain damaged tissues in joints of vertebrates. In U.S. Pat. No. 5,922,692, Marino discloses that glucosamine sulfate and chondroitin sulfate can be added to foodstuffs. Lexington, Ky.) for oral administration of hyaluronic acid.

Other products for parenteral administration include e.g., chondroitin sulfate for intramuscular use available from Syntex S. A. Argentina; polysulfated glycosaminoglycan (PS-GAG) for intra-articular and intramuscular injection which is available as ADEQUAN®. from Luitpold Pharmaceuticals, Inc., Shirley N.Y. and N-acetyl glucosamine for intramuscular or intra-articular injection (see U.S. Pat. No. 3,697,652 to Rovati et al.). Each of the afore-mentioned preparations has met with varying degrees of success and many, particularly HA and PSGAG still enjoy widespread use in the treatment and prevention of DJD in man and in animals. The risks and rewards and overall benefit of certain of these treatment modalities is controversial, however, as evidenced e.g., by "Hyaluronic Acid Rules in Severe Joint Problems", HORSE JOURNAL, Vo. 9, No. 5 pp. 3-6, May 2002.

More importantly, prior to the present invention there has not been a single effective composition specifically formulated for intra-articular use which combines an optimal combination of active agents which can be used for intra-articular treatment of OA and/or DJD. In particular, there exists a need in the art for a composition formulated for intra-articular use which However, despite the relative commercial success of many of the "nutraceutical" preparations, controversy abounds as to their relative levels of effectiveness in actually preventing or treating damage to articular cartilage and/or DJD. For example, one study conducted by Luitpold Pharmaceutical, Inc. found that no anti-inflammatory or chondroprotective effect could be demonstrated when oral glucosaminoglycans (GAG's) were used to treat equine DJD.

Numerous parenteral intra-articular and systemic (intramuscular and intravenous) approaches to therapy have also been tried. For example, hyaluronate sodium (hyalurionic acid or "acid") has been used extensively as an intra-articular and intravenous treatment for human and animal joint disease. LEGEND®, for example, available from Bayer Corporation in Shawnee Mission, Kans., is approved for both intravenous and intra-articular use in the horse. U.S. Pat. No. 4,782,046 to Brown et al. describes an ultrapure form of hyaluronic acid prepared from group C streptococcal organisms. U.S. Pat. No. 4,808,576 to Schultz et al. disclose methods of administration of hyaluronic acid other than intra-articularly, e.g., intramuscularly or topically. Recently, there has even been a product introduced, CONQUER™ (Kinetic Technologies, Inc., uniquely combines synergistically active agents for use as a adjunct to surgical intervention, e.g., as a joint lavage and/or post surgical treatment. There is especially a need in the art for a composition which can be used during and post surgically to aid in the physical removal (lavage) of detrimental and degenerative post surgical joint debris, while simultaneously acting to lubricate joint surfaces, protect the remaining articular cartilage from further enzymatic degradation and provide in situ "fuel" for synoviocyte and chondrocyte production of endogenous hyaluronan and proteoglycans.

Likewise, prior to the present invention there has not been a single effective composition specifically formulated for intra-articular use and/or parenteral (e.g., intravenous or intramuscular) use which combines an optimal combination of active agents which can be used for intra-articular and/or parenteral treatment of traumatic synovitis. In particular, there exists a need in the art for a composition formulated for intra-articular use or systemic use which combines synergistically active agents to treat and/or prevent traumatic synovitis.

SUMMARY OF THE INVENTION

A primary object of the present invention is to provide a composition and related method for treatment and/or prevention of articular cartilage damage, especially post surgically, by providing a composition adapted for intra-articular use which can be used as a joint lavage to remove post surgical joint debris while simultaneously producing a chondroprotective effect for the remaining articular cartilage of the joint and facilitating nutrient transfer within the cells of the articular cartilage and promoting regeneration of needed components such as hyanuronan and proteoglycans. One embodiment of the present invention is therefore directed to a composition and a method to accelerate the process of articular cartilage repair and regeneration in diathrodial joints, especially in post surgical applications.

In one embodiment for the treatment and/or repair of damage to the articular cartilage, the invention provides a composition for intra-articular injection or systemic use comprised of therapeutic amounts of: chondroitin sulfate and hyaluronan (hyaluronic acid).

The compositions of one embodiment of the invention provide a chondroitin sulfate, (as CS4 and/or CS6) adapted for intra-articular injection which acts to stimulate the production of proteoglycans, glycosaminoglycans, and collagen, inhibit degenerative enzymes excreted by the chondrocytes, and synoviocytes, and to aid in nutrient transportation within the synovial fluid. The chondroitin sulfate of the compositions provided herein is preferably in solution or suspension with hyaluronan. The exogenous hyaluronan comprising the compositions provided herein acts to replace depleted endogenous HA and to lubricate and coat healthy as well as damaged articular tissue during the reparative process.

In certain embodiments of the invention, the compositions adapted for intra-articular and/or other parenteral use may further optionally include N-acetyl D-glucosamine. The N-acetyl D-glucosamine provided in the compositions of the invention increases the synoviocyte and chondrocyte production and subsequent availability of endogenous hyaluronan within the joint and cartilage matrix by the direct in situ inclusion of its prime substrates galactosamine (through chondroitin sulfate assimilation) and N-Acetyl D-glucosamine.

Another object of the present invention is to provide a composition and related method for treatment and/or prevention of traumatic synovitis and thereby prevent the onset of degenerative joint disease, by providing a composition adapted for intra-articular use and/or parenteral use which, e.g., has positive anti-inflammatory effects on the synovial membrane of a traumatized joint and/or acts to maintain mechanical homeostasis by, e.g., increasing fluid outflow buffering within the joint. Another object of the invention is to provide a composition and method that has the advantage of treating or preventing traumatic synovitis of multiple joints with a single parenteral (e.g. intravenous or intramuscular) injection of a therapeutic amount of the composition.

In yet another embodiment for the prevention and/or treatment of traumatic synovitis, the invention provides a composition adapted for intra-articular and/or systemic or parenteral administration comprised of therapeutic amounts of: chondroitin sulfate and hyaluronan (hyaluronic acid). Systemic administrations can include but are not limited to intramuscular, intravenous or subcutaneous injection.

The compositions of the invention provide a glycosaminoglycans, specifically chondroitin sulfate, (as CS4 and/or CS6) adapted for intra-articular and/or parenteral injection which acts to stimulate the production of hyaluronic acid, inhibit degenerative enzymes excreted by the chondrocytes, and synoviocytes, and to aid in decreasing the presence of inflammatory mediators within the synovial fluid. The chondroitin sulfate of the compositions provided herein is preferably in solution or suspension with hyaluronan. The exogenous hyaluronan comprising the compositions provided herein acts to replace depleted endogenous HA and to lubricate and coat healthy as well as damaged articular cartilage but also to reduce inflammation of synovial membranes to treat and/or prevent traumatic synovitis.

DETAILED DESCRIPTION OF THE INVENTION

Additional objects, advantages and other novel features of the invention will be set forth in part in the description that follows and in part will become apparent to those skilled in the art upon examination of the foregoing or may be learned with the practice of the invention. Additionally, throughout this document, various publications and patents have been cited, the contents of which are incorporated herein by reference in their entirety.

Set forth in greater detail below are specific details related to novel compositions and methods for treatment and/or prevention of damage to articular cartilage in man and in animals. In particular, the present invention provides specific teachings related to novel compositions and methods for intra-operative or post surgical intra-articular treatment of osteoarthritis and degenerative joint disease in the subject surgical animal. In addition, the present invention provides compositions and surprisingly novel methods for the parenteral (systemic) treatment and/or prevention of synovitis, e.g., traumatic synovitis due to mild injury or stress. The examples set forth herein are in no way intended to limit the scope of the invention. Those of skill in the art will realize that, given the teachings provided herein, many variations of the methods are possible that will fall within the scope of the of the invention.

In one embodiment, the invention provides a composition adapted for intra-articular injection, that is useful for the treatment and/or prevention of damaged articular cartilage of diarthrodial joints, the composition comprising therapeutic amounts of: chondroitin sulfate; hyaluronan and may optionally include N-acetyl D-glucosamine. In particular, the compositions of certain embodiments of the invention are adapted for use as an intra-articular joint lavage for use during and/or following surgery (arthrotomy or arthroscopic surgery) of the joint.

The glucosaminoglycans present in the compositions provided herein help to contribute to the return of homeostasis of the joint through the increase in the glucosaminoglycan pool used by chondrocytes for proteoglycan synthesis. In addition to that effect, the incorporation of chondroitin sulfate into the compositions provided herein helps slow down the inflammatory process, acting directly on the enzymes and inflammatory mediators that are released when inflammation is present. The sodium hyaluronate (hyaluronan) provided by the compositions serves to cover the surface of the joint capsule and articular cartilage with a thin coating to aid in resistance to cartilage compression while retaining elasticity, it also interacts with proteoglycans to form a stabile aggregate, as well as providing lubricating properties. Hyaluronan also directly aids in the removal of waste products from the joint capsule and acts as an inhibitor of inflammatory mediators (see, "Hyaluronan and its Use in the Treatment of Equine Joint Disease", Howard & Mcllwraith pp. 257-269, in JOINT DISEASE IN THE HORSE", W. B. Sanders, 1996 (ISBN 0-7216-5135-6)).

The compositions of the invention provide a unique mixture comprised of the naturally occurring glucosaminoglycans: chondroitin sulfates CS4 and CS6, and hyaluronan (hyaluronic acid). Glucosaminoglycans are polysaccharides which occur widely in the animal kingdom. Glucosaminoglycans that are present in the tissues of vertebrate animals have mainly a linear structure which is repetition of a disaccharide units composed of two monosaccharides. Five kinds of glucosaminoglycans are found in the tissues and fluids of vertebrates: chondroitin sulfates, keratin sulfates, dermatin sulfates, heparin sulfates; hyaluronic acid and heparin.

Chondroitin sulfates are one critical component of certain embodiments of the compositions of the invention. In general, chondroitin sulfates are widely found in the connective tissues of animals in two forms of repeating disaccharides of D-glucouronic acid and N-acetyl galactosamine: CS4 sulfate where n-acetyl galactosamine holds an ester sulfate in its CS4 position or CS6 sulfate where the ester sulfate is in the CS6 position. Both CS4 and CS6 chondroitin sulfate function in the articular matrix as a major constituent. Chondroitin sulfates contribute to keep the cartilage matrix's normal characteristics through the increase of the glucosaminoglycan pool used by the chondrocytes for proteoglycan synthesis, as well as slowing down the inflammatory process acting directly on the enzymes inhibiting the compliment cascade and by exhibiting anti-prostoglandin activity.

In particular, chondroitin sulfate is a long hydrophilic chain of repeating sugars. This glycosaminoglycan binds to proteoglycan molecules aiding in water and nutrient transportation within the articular cartilage. Chondroitin in its sulfate form includes galactosamine, a primary substrate of hyluronan and a disaccharide pathway for proteoglycan synthesis secondary to the hexosamine pathways utilized for glycosaminoglycan production. Chondroitin sulfate chains comprise the space formation of the cartilage matrix and integral parts of the proteoglycan molecule. Chondroitin stimulates the production of proteoglycans, glycosaminoglycans, and collagen, which are the building blocks of healthy cartilage. Chondroitin sulfate also inhibits the secretion of degenerative enzymes by the chondrocytes within articular cartilage. Chondroitin Sulfates are non-toxic and work synergistically with glucosamine to hydrate and repair articular cartilage. Chondroitin sulfate also works synergistically with hyaluronic acid to increase viscosity of synovial fluid and increase outflow buffering within the joint. (see, Hyaluroninin Synovial Joints: Molecular Sieving, Concentration Polarization & Secretion Regulation in vivo" Coleman et al., Matrix Biology Institute 2004).

Another critical component of certain embodiments of the compositions of the invention, sodium hyaluronate, is a natural constituent of connective tissues and synovial fluid composed of repeating disaccharide units each consisting of D-glucouronic acid and N-acetyl D-glucosamine. Within the joint capsule, the surface of articular cartilage is covered by a thin layer of sodium hyaluronate. It specifically interacts with cartilage proteoglycans to form a stabile aggregate. Within the synovial fluid it confers viscal elasticity as well as lubricating properties. Hyaluronan aids in providing nourishment and waste removal from the articular matrix. It also provides biochemical activity to help prevent excess fibrous tissue from forming in the cartilage matrix. When combined with chondroitin sulfate, the exogenous hyaluronin present in the compositions of the invention acts synergistically with the chondroitin sulfate to aid in the treatment and/or prevention of traumatic synovitis and/or damage to articular cartilage.

Therefore, one embodiment of the invention provides a composition adapted for intra-articular or other parenteral injection that is useful for the treatment and/or prevention of traumatic synovitis and/or damaged articular cartilage of diarthrodial joints, the composition comprising therapeutic amounts of: chondroitin sulfate and hyaluronan in the substantial absence of other naturally occurring or synthetic chondroprotective agents, e.g., other glycosaminoglycans and/or proteoglycans that are known to those skilled in the art as set forth, e.g., in US Patent Application US 2001/0046971 to Hammerly etc.

In general, the compositions of certain embodiments of the invention may optionally include N Acetyl D-glucosamine, which is a compound necessary for cartilage matrix synthesis as it enhances chondrocyte synthesis of glucosaminoglycans. N-Acetyl D-glucosamine also possesses the ability to enhance synthesis of key components of synovial fluid by feeding both reactions necessary for the production of hyaluronan as well as for proteoglycans. Therefore, by replacing specific glucosaminoglycans lost by the invasion of the diarthrodial joint during surgery and also providing the key molecules to enhance and promote the restoration of normal hyaluronan and proteoglycan synthesis, the physician or veterinarian can be assured of the composition's capability to protect the joint as well as to aid in the healing process.

N-Acetyl D-Glucosamine is also a derivative of glucose obtained by chemical hydrolysis of chitin. This polysaccharide is readily soluble in water and extremely bioavailable. N-Acetyl D-glucosamine binds to glucuronic acid as well as galactose making it a precursor to hyaluronic acid, keratansulfate and chondroitin sulfate. This unique derivative aids a proteoglycan, collagen and glycosaminoglycan production. N-acetyl D-glucosamine has also been shown to aid in the healing of soft tissue injury.

The embodiments of the presents invention have are safe and non-toxic in the therapeutic amounts as set forth herein.

Each embodiment provides a specific benefit in relation to the repair and regeneration of articular cartilage and in protection of existing articular cartilage. Thus, it can be realized that certain of the compositions of this invention, e.g., those comprised of chondroitin sulfate, N-acetyl D-glucosamine and hyaluronic acid provide a unique combination for intra-articular use of replacement components and metabolic precursors which advantageously stimulate the production of glycosaminoglycans including hyaluronic acid, proteoglycans and collagen, thereby assisting the body's natural repair mechanisms and specifically directing the chondrocytes in the production of new articular cartilage.

Another important aspect of the compositions of the invention is that they are adapted for intra-articular use and are especially well suited for use as a "medical device" for physical lavage or flushing of the diarthrodial joint during and/or post surgery. The highly negative ionic charge and unique characteristics of the compositions set forth herein act to directly trap or bind positively charged particles present in the joint, e.g., surgical debris and free radicals released from the inflammatory processes, and physically remove such particles from the joint fluid. Because of their capacity for multidimensional disposition, hydrophilic nature, prominent presence of negative charges and lubricating capabilities, the compositions provided herein also exhibit selective permeability, water retention, elasticity and support to compression, which are essential characteristics to aid the return of the diathrodial joint to homeostasis.

Thus, in one embodiment, the compositions of the invention have been specially adapted for intra-articular use and/or parenteral (e.g., intravenous or intramuscular) are sterile solutions or suspensions comprised of therapeutic amounts of chondroitin sulfate and hyaluronan. In addition to the aforementioned active agents, it can be appreciated by one of skill in the art that the compositions of the invention which are adapted for intra-articular use can also comprise preservatives, pharmaceutically active carriers, excipients, stabilizers, buffers, antimicrobial growth inhibitors and the like and the use of such is contemplated by the invention.

It is contemplated by the invention that the compositions provided herein may be useful in methods for the intra-articular and/or parenteral (systemic) treatment and/or prevention of any damage or potential damage to articular cartilage including, but not limited to, mild cases of stress and joint capsule inflammation or synovitis (e.g., traumatic synovitis, which if left untreated can led or progress into articular cartilage damage), osteoarthritis, osteochondrosis dessicans (OCD), traumatic injury, fractures, degenerative joint disease (DJD) and septic arthritis. However, one presently preferred use for the compositions of the invention is in a method of intra-operative and/or post-surgical joint lavage or in treatment and/or prevention of further cartilage damage, e.g., post surgical DJD.

In surgery, e.g., arthroscopic surgery for removal of an intra-articular cartilage flap, OCD lesion, subchondral bone cyst or chip fracture, there is a loss of synovial fluid, proteoglycan concentration and constituting glucosaminoglycans with the subsequent loss of the above-mentioned desirable characteristics provided by healthy synovial fluid. Likewise, surgical intervention (the result of "the three T's", time, trash, and trauma), in and of itself, causes inflammation that, in turn, produces inflammatory exudates with an increase in the enzymatic activity and inflammatory mediators within the affected joint.

During surgery, e.g., for removal of a cartilage flap or chip fracture, microscopic fragments of cartilage and/or other tissue such as subchondral bone fragments, hemorrhage etc. are released into the joint. It is desirable that such "surgical debris" be flushed or lavaged out of the joint. Likewise, during surgery, especially during arthroscopic surgery, the surgeon's field of vision often becomes clouded or obstructed with surgical debris, hemorrhage etc. and constant lavage under pressure is required for visualization of the surgical field. Thus, one embodiment of the invention provides a sterile composition that is adapted for direct intra-articular use as an intra operative lavage or which can be added to a preselected lavage fluid (e.g., lactated ringers, or normal saline) to provide concurrent therapeutic benefit of the active agents while the joint is being lavaged with the preselected fluid.

In one embodiment the compositions of the invention are comprised of therapeutic amounts of chondroitin sulfate and hyaluronan (hyaluronic acid). It is presently preferable that the compositions of the invention are sterile solutions and/or are suspensions comprised of chondroitin sulfate and hyaluronan. However, it is contemplated that other formulations are possible and are within the scope of the invention, e.g., a powdered formulation suitable for reconstitution with a suitable injectable liquid or for addition to a preselected lavage fluid. In particular, it can be appreciated by one of skill in the art that the active agents of the compositions can be stored in a freeze dried or lyophilized state for reconstitution and use at a desired time.

A presently preferred embodiment of the invention comprises a composition adapted for intra-articular and/or parenteral administration comprised of chondroitin sulfate and hyaluronan wherein the therapeutic amount of chondroitin sulfate is from between about 0.5 grams to about 1.5 grams of a suitable chondroitin sulfate per unit dose of the composition. In one embodiment, the therapeutic amount comprises about 1 gram of CS4 chondroitin sulfate, or about 1 gram of CS6 chondroitin sulfate or about 1 gram of a mixture of CS4 and CS6 chondroitin sulfate per unit dose. In another embodiment, the therapeutic amount of chondroitin sulfate is about 1 gram of chondroitin sulfate comprised of about 40% CS4 chondroitin sulfate and about 60% CS6 chondroitin sulfate.

Presently preferred therapeutic amounts of hyaluronan include from about 10 mg to about 50 mg of hyaluronan per unit dose of the composition. An especially preferred therapeutic amount of hyaluronan from about 20 to about 40 mg of hyaluronan per unit dose of the composition.

It can be appreciated by one of skill in the art that the hyaluronan can be selected from among any of a number of commercially available sources such as commercially available Sodium Hyaluronate. Likewise there are numerous commercially available sources of N acetyl D-glucosamine and Chondroitin Sulfate that are available for use in the compositions set forth herein.

In certain embodiments of the invention the compositions may optionally include therapeutic amounts of N acetyl D-glucosamine for the compositions of the invention that are from about 0.5 grams to about 1.5 grams of N acetyl D-glucosamine per unit dose. An especially preferred therapeutic amount of N acetyl D-glucosamine is about 1 gram of N acetyl D-glucosamine per unit dose of the composition.

Another presently preferred embodiment of the invention provides a composition adapted for intra-articular and/or parenteral injection comprised of a sterile solution or suspension comprised of about 1 gram of chondroitin sulfate as a mixture of about 40% CS4 and 60% CS6 chondroitin sulfate; and about 20-40 mg but especially about 30 mg of hyaluronan (e.g., Na Hyaluronate) per unit dose of the composition.

One example of a preferred embodiment of the invention comprises a 10 ml unit dose of the composition. The composition is made as follows. One gram of chondroitin sulfate powder is admixed with 2 ml of a 10 mg/ml solution of sodium hyaluronate. The resultant mixture of chondroitin sulfate and sodium hyaluronate is qs with approximately 10 ml of bacteriostatic water to achieve a final volume of 10 ml. The final concentration of chondroitin sulfate in the composition is 0.1 gram/ml or 10% and the final concentration of sodium hyaluronate in the composition is 00.2 gm/ml or 20%.

One presently preferred embodiment of the invention provides a composition adapted for intra-articular and/or parenteral administration which consists essentially of therapeutic amounts of chondroitin sulfate and hyaluronan.

In another embodiment the invention provides a composition adapted for intra-articular and/or parenteral administration which comprises therapeutic amounts of chondroitin sulfate; and hyaluronan wherein the molecular weight per unit dose of the composition is from between about 450,000 Daltons to about 1,100,000 Daltons. In yet another embodiment the invention provides a composition adapted for intra-articular and/or parenteral administration which comprises therapeutic amounts of chondroitin sulfate; and hyaluronan wherein the molecular weight per unit dose of the composition is from between about 500,000 Daltons to about 1,000,000 Daltons. In yet another embodiment the invention provides a composition adapted for intra-articular and/or parenteral administration which comprises therapeutic amounts of chondroitin sulfate and hyaluronan wherein the molecular weight per unit dose of the composition is from between about 550,000 Daltons to about 700,000 Daltons but is especially about 600,000 Daltons.

In a preferred embodiment the invention provides a composition adapted for intra-articular and/or parenteral administration which comprises therapeutic amounts of chondroitin sulfate and hyaluronan wherein the molecular weight per unit dose of the composition is greater than about 450,000 Daltons. In another embodiment, the invention provides a composition adapted for intra-articular and/or parenteral administration which comprises therapeutic amounts of chondroitin sulfate and hyaluronan wherein the molecular weight per unit dose of the composition is greater than about 550,000 Daltons.

In yet another embodiment of the invention the compositions set forth herein can further comprise a therapeutic amount of a suitable antibiotic. Suitable antibiotics for use in the compositions provided herein include, but are not limited to any of the antibiotics that can be adapted for intra-articular use, (see, e.g., "Infectious Arthritis" Alicia L. Bertone, pp. 397-409, in JOINT DISEASE IN THE HORSE", W. B. Sanders, 1996 (ISBN 0-7216-5135-6)). As can be appreciated by one of skill in the art, the choice of antibiotic and therapeutic amount can depend many factors including, but not limited to, e.g., the etiology of the infectious organism being treated or personal preference of the treating veterinarian or physician.

The compositions of the invention can also further comprise other therapeutic agents insofar as it is generally used as a therapeutic for joint disease (arthropathy). Examples of other such therapeutic agents include, but are not limited to, synthetic and non-synthetic corticosteroid agents, nonsteroidal anti-inflammatory drugs, antirheumatics, immunoregulators, immunosuppressors, articular function augmenters, and interleukin production inhibitors. Specific examples of corticosteroid agents include, but are not limited to dexamethasone, hydrocortisone, triamcinolone, betamethasone, predonisolone, methylpredonisolone, halopredone, beclomethasone and the like.

Specific examples of non-steroidal anti inflammatory agents include, but are not limited to diclofenac, indometha-cin, ibuprofen, ketoprofen, aspirin, diflunisal, fulfenamic acid, floctafenine, tolfenamic acid, sulindac, fenbufen, salicylic acid, acemetacin, proglumetacin, nabumetone, protizinic acid, thiaprofen, oxaprozin, loxoprofen, alminoprofen, zaltoprofen, flurbiprofen, flurbiprofen and the like.

In one embodiment, the compositions of present invention can further comprise of at least one pyrazolyl benzenesulfonamide compound, e.g., as set forth in U.S. Pat. No. 5,756,529 and U.S. Pat. No. 5,466,823, the contents of which is incorporated herein by reference. In particular, the compositions of the invention can further comprise a diaryl substituted pyrazole useful for treatment of inflammation and/or pain. It is specifically contemplated that the compositions of the invention can further comprise therapeutic amounts of any of the class of diaryl substituted pyrazoles their isomers, analogs and/or metabolites. In particular, these compounds reduce inflammation and/or pain primarily via inhibition of cyclooxygenase-2 (COX-2). In a preferred embodiment of the invention, the compositions provided further comprise a non-steroidal agent that reduces inflammation and/or pain primarily via inhibition of cyclooxygenase-2 (COX-2) and with the substantial absence of inhibition of cyclooxygenase-1 (COX-1). Examples of suitable diaryl substituted pyrazoles for use in the compositions of the invention, include but are not limited to celecoxib, rofecoxib and the like.

Examples of other agents which may be added to the core compositions set forth herein include, axetil, piroxicam, tenoxicam, ampiroxicam, meloxicam, D-penicillamine, bucillamine, gold sodium thiomalate, auranofin, lobenzarit, salazosulfapyridine, methotrexate, cyclophosphamide, azathioprine, mizoribine, cyclosporin and the like.

In a particularly preferred embodiment, the invention also provides a composition adapted for intra-articular administration comprised of therapeutic amounts of chondroitin sulfate; hyaluronan and a suitable antioxidant or free radical scavenger. In one embodiment, the compositions of the invention can further comprise a therapeutic amount of suitable superoxide dismutase (SOD) or other antioxidant including, but not limited to, examples set forth in U.S. Pat. No. 6,127,356 to Crapo et al., the contents of which are incorporated herein by reference.

In another embodiment, the invention provides a composition adapted for parenteral administration, that is useful for the treatment and/or prevention of traumatic synovitis, the composition comprising therapeutic amounts of: chondroitin sulfate and hyaluronan. In another embodiment, a related method of treatment and/or prevention of synovitis in an animal is provided which comprises parenterally administering a therapeutic amount of a composition comprised of chondroitin sulfate and hyaluronan to the animal. In particular, the invention provides the surprising discovery of a synergistic effect provided by the combination of the active agents of the compositions of the invention in the treatment of traumatic synovitis when the compositions are administered parenterally, e.g., intravenous administration.

The foregoing description of preferred embodiments of the invention have been presented for purposes of illustration and description. They are not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. A composition adapted for parenteral administration for treatment of a damaged joint in man or in animals, the composition consisting essentially of therapeutic amounts of: chondroitin sulfate, hyaluronan, and N-acetyl D-glucosamine, wherein said damaged joint is caused by a disease or condition selected from inflammation, synovitis, inflammatory arthritis, osteoarthritis, osteochondrosis dessicans (OCD), traumatic injury, fractures, surgical trauma or injury, degenerative joint disease (DJD), or septic arthritis.

2. A method for treatment of a damaged joint in man or in animals, comprising parenterally administering a therapeutic amount of a composition consisting essentially of chondroitin sulfate, hyaluronan, and N-acetyl D-glucosamine, and wherein said damaged joint is caused by a disease or condition selected from inflammation, synovitis, inflammatory arthritis, osteoarthritis, osteochondrosis dessicans (OCD), traumatic injury, fractures, surgical trauma or injury, degenerative joint disease (DJD) or septic arthritis.

3. The composition of claim 1, wherein the therapeutic amount of N-acetyl D-glucosamine is from about 0.5 grams to about 1.5 grams of N-acetyl D-glucosamine per unit dose of the composition.

4. The composition of claim 1, wherein the therapeutic amount of chondroitin sulfate comprises from between about 0.5 grams to about 1.5 grams of a suitable chondroitin sulfate per unit dose of the composition, and wherein the suitable chondroitin sulfate is CS4 chondroitin sulfate, CS6 chondroitin sulfate, or a mixture of CS4 chondroitin sulfate and CS6chondroitin sulfate.

5. The composition of claim 1, wherein the therapeutic amount of hyaluronan is from about 10 mg to about 50 mg of hyaluronan per unit dose of the composition.

6. The method of claim 2, wherein the therapeutic amount of N-acetyl D-glucosamine is from about 0.5 grams to about 1.5 grams of N-acetyl D-glucosamine per unit dose of the composition.

7. The method of claim 2, wherein the therapeutic amount of ehondroitin sulfate comprises from between about 0.5 grams to about 1.5 grams of a suitable chondroitin sulfate per unit dose of the composition, and wherein the suitable chondroitin sulfate is CS4 chondroitin sulfate, CS6 chondroitin sulfate, or a mixture of CS4 chondroitin sulfate and CS6 chondroitin sulfate.

8. The method of claim 2, wherein the therapeutic amount of hyaluronan is from about 10 mg to about 50 mg of hyaluronan per unit dose of the composition.

9. The method of claim 2, wherein the therapeutic composition is administered intramuscularly, intravenously, intraarticularly, subcutaneously, or systemically.

* * * * *

UNITED STATES PATENT AND TRADEMARK OFFICE
CERTIFICATE OF CORRECTION

| | | |
|---|---|---|
| PATENT NO. | : 7,485,629 B2 | Page 1 of 1 |
| APPLICATION NO. | : 11/015137 | |
| DATED | : February 3, 2009 | |
| INVENTOR(S) | : Frank D. Marcum | |

It is certified that error appears in the above-identified patent and that said Letters Patent is hereby corrected as shown below:

At column 14, line 5, delete "CS6chondroitin" and insert --CS6 chondroitin--.

At column 14, line 14, delete "ehondroitin" and insert --chondroitin--.

Signed and Sealed this

Seventeenth Day of March, 2009

JOHN DOLL
*Acting Director of the United States Patent and Trademark Office*